*(12)* United States Patent
Stark et al.

*(10)* Patent No.: US 8,072,602 B2
*(45)* Date of Patent: Dec. 6, 2011

(54) COMBINATION OF READER AND INCUBATOR

(75) Inventors: Jacobus Stark, Rotterdam (NL); Pieter Cornelis Langeveld, Delft (NL); Bastiaan Groen, Dordrecht (NL); Tim de Graaf, Zoetermeer (NL); Willem Plugge, Delfgauw (NL)

(73) Assignee: DMS IP Assets B.V., Heerlen (NL)

( * ) Notice: Subject to any disclaimer, the term of this patent is extended or adjusted under 35 U.S.C. 154(b) by 575 days.

(21) Appl. No.: 12/278,333

(22) PCT Filed: Feb. 7, 2007

(86) PCT No.: PCT/EP2007/001159
§ 371 (c)(1),
(2), (4) Date: Dec. 15, 2008

(87) PCT Pub. No.: WO2007/090683
PCT Pub. Date: Aug. 16, 2007

(65) Prior Publication Data
US 2009/0306905 A1   Dec. 10, 2009

(30) Foreign Application Priority Data
Feb. 8, 2006 (EP) .................................. 06101411
Apr. 25, 2006 (EP) .................................. 06113088

(51) Int. Cl.
*G01N 21/25* (2006.01)
(52) U.S. Cl. ................................................. 356/402
(58) Field of Classification Search ............... 356/402
See application file for complete search history.

(56) References Cited

U.S. PATENT DOCUMENTS

| | | | |
|---|---|---|---|
| 5,783,154 A | 7/1998 | Althainz et al. | |
| 2002/0064867 A1* | 5/2002 | Clark et al. | 435/288.7 |
| 2003/0111607 A1* | 6/2003 | Bachur et al. | 250/343 |
| 2004/0038390 A1* | 2/2004 | Boege et al. | 435/288.7 |
| 2004/0185552 A1 | 9/2004 | Griner et al. | |
| 2005/0266516 A1* | 12/2005 | Kanipayor et al. | 435/34 |

FOREIGN PATENT DOCUMENTS

| | | |
|---|---|---|
| DE | 40 03 604 | 8/1991 |
| EP | 0 936 461 | 8/1999 |
| WO | 99/32656 | 7/1999 |
| WO | 03/033728 | 10/2002 |
| WO | 2005/005656 | 1/2004 |
| WO | 2005/118837 | 12/2005 |

OTHER PUBLICATIONS

International Search Report for PCT/EP2007/001159, mailed Apr. 2, 2007.

* cited by examiner

*Primary Examiner* — Kara E Geisel
(74) *Attorney, Agent, or Firm* — Baker Donelson, Bearman, Caldwell & Berkowitz, PC

(57) ABSTRACT

A detection arrangement for detecting presence of an analyte in a sample includes a processor, a memory, a display, a color measuring device, and a temperature controller for maintaining a constant temperature or a temperature profile of the sample. A method is also provided for determining the presence or absence of an analyte in a fluid by analysis of image data from an assay that generates an image result on an assay medium.

6 Claims, 11 Drawing Sheets

COMBINATION OF READER AND INCUBATOR

This application is the U.S. national phase of International Application No. PCT/EP2007/001159, filed 7 Feb. 2007, which designated the U.S. and claims priority to Europe Application Nos. 06101411.4, filed 8 Feb. 2006 and 06113088.6, filed 25 Apr. 2006, the entire contents of each of which are hereby incorporated by reference.

FIELD OF THE INVENTION

The present invention relates to an improved novel assay system and a new method for the rapid determination of the presence or absence of analytes in a sample using simple reading- and computer equipment combined with heating equipment.

BACKGROUND OF THE INVENTION

Test methods (assays) for the detection of analytes in samples are widely known in the art. Particular examples of assays are those whereby the analyte to be detected has a specific color-, IR-, or UV-spectrum and can thus be detected by means of a reader comprising a photoelectric cell, a scanner, any type of camera and of course visually. If the spectral characteristics of the analyte in question are not sufficient for adequate detection it is often possible to use indirect methods. For instance, methods are available whereby the presence of the analyte triggers a secondary process, which then results in the formation of a product or event having a specific spectral characteristic. This may be a colored product, but can also be a change in pH, redox-potential, temperature and the like, which in turn triggers an indicator molecule to change color-, IR-, redox- or UV-spectrum. Many types of secondary processes are employed in the art for various applications.

One example is a chemical reaction of the analyte with a fluorescent or colored molecule resulting in a product without fluorescence or color or with a different fluorescence or color, or the other way around.

Another example is inhibition of a (bio) chemical process by the analyte whereby the presence of the analyte is indirectly measured as a result of the absence (or presence) of the effect of that (bio) chemical process. The latter may be illustrated by, for instance, microbiological assays for the detection of analytes, particularly residues of antibiotics and chemotherapeutics, in fluids such as milk, meat juice, serum, urine, (waste) water and the like. Examples of such assays have been described in CA 2056581, DE 3613794, EP 0005891, EP 0285792, EP 0611001, GBA 1467439 and U.S. Pat. No. 4,946,777. These descriptions all deal with ready to use assays that make use of an assay organism and will give a result by the change indicated by an indicator molecule, for instance a change of color of a pH- and/or redox-indicator, added to the assay. A change in the indicator indicates the presence of a growing assay organism. The principle is that when an analyte is present in a fluid in a concentration sufficient to inhibit growth of the assay organism, the color of the indicator will stay the same. In contrast, when no inhibition occurs, growth of the assay organism is accompanied by the formation of acid or reduced metabolites or other phenomena that will induce an indicator signal. The known assays mentioned above include an assay medium, such as an agar medium, inoculated with a suitable assay organism, preferably a strain of *Bacillus, Escherichia* or *Streptococcus*, and a pH indicator and/or a redox indicator. The suitable assay organism and the indicator, and optional buffers, nutrients, surfactants and the like, are introduced into a gel or simply kept in solution. Normally conditions are chosen in such a way that the assay organisms stay alive but cannot multiply because of lack of an essential growth requirement (this may be a nutrient, a specific pH- or temperature value or any other essential parameter).

Assays that require a more or less stringent temperature regime for the results to be generated reliably and accurately form a special class of methods amongst the ones mentioned above. These types of methods require incubation equipment in order to maintain the assay at a predetermined temperature or temperature profile for a given period of time. Usually the result of such an assay is determined afterwards by using a reader equipped to detect the event that indicates the presence of the analyte. An example of such an assay is described in WO 03/033728 dealing with a method for detecting the presence of an analyte (such as a β-lactam) in a sample (such as food products, e.g. meat, milk, or body fluids, e.g. blood, urine) following incubation at 64° C. by determining color values of the sample, associated with the L*a*b color model, using a standard scanner coupled to a computer. The latter reading technology was also disclosed in EP 953 149.

A severe disadvantage of these prior art methods is that it is only possible to perform reading operations after incubation. As a result of this, diagnostic methods such as microbiological assays for the detection of antimicrobial residues only give a positive or negative result (i.e. merely indicate whether or not the concentration of analyte is above or below a certain threshold value). In case of a positive result obtained with these so-called screening assays, the sample has to be examined further for confirmation using a second diagnostic method. Mostly, such confirmation methods, e.g. HPLC or mass spectrometry, are extremely expensive and it takes a long time before the results are known. Thus, reading assay results during the screening assay itself would be advantageous, as this would give access to more detailed information that could improve on parameters such as assay duration, type of analyte or concentration of analyte.

Nevertheless, reading of information during an assay and simultaneous incubation of such an assay is known in methods based on the presence of a light source on one end of the assay and collecting light signals on the other end of the assay, an example of which are the well-known ELISA-readers. This principle has, unfortunately, three major disadvantages. Firstly, in assays wherein the sample is placed on a substrate and the required reaction takes place within the substrate, the nature and amount of the sample will disturb the measurement when light or another type of radiation travels through both sample and substrate. Secondly, the equipment usually employed for such measurements is mostly dedicated and designed for trained personnel and to be used in a laboratory environment. Thirdly, the prior art principles are designed to measure one particular wavelength only. There is thus a need for equipment and methods that do not suffer from these drawbacks.

SUMMARY OF THE INVENTION

It is an object of the present invention to provide a detection arrangement for detecting presence of an analyte in a sample, comprising a processor, a memory, a display, and a color measuring device, said memory, said display and said color measuring device being arranged to communicate with said processor, said color measuring device being arranged to generate light signals, to send said light signals to said sample, to receive return light signals from said sample, to convert said return light signals into color signals and to send said color signals to said processor, said processor being operated by instructions stored in said memory and being arranged to calculate a value of a composite parameter Z in accordance with a following equation:

$$Z = \sum_{i=1}^{n} w_i x_i$$

where $x_i$ is a color signal i and $w_i$ is a corresponding weighing factor and i is an index ranging from 1 to n and n is an integer equal to the number of color signals, characterized in that a means is present for maintaining a constant temperature or a temperature profile of said sample.

Furthermore, it is an object of the present invention to provide a method for determining the presence or absence of an analyte in a fluid by analysis of image data from an assay that generates an image result on an assay medium, comprising the steps of:

(a) incubating a sample of said fluid together with said assay at a pre-set temperature or temperature profile
(b) obtaining said image result on an assay medium; and
(c) imaging the image result with an image acquisition device to generate digital image data corresponding to the image result; and
(d) using data processing means, applying to the digital image data a stored relationship between the image result and assay calibration data to generate a quantified result for said assay, characterized in that incubation step (a) is carried out simultaneously with steps (b)-(c).

DETAILED DESCRIPTION OF THE INVENTION

Figure 1:
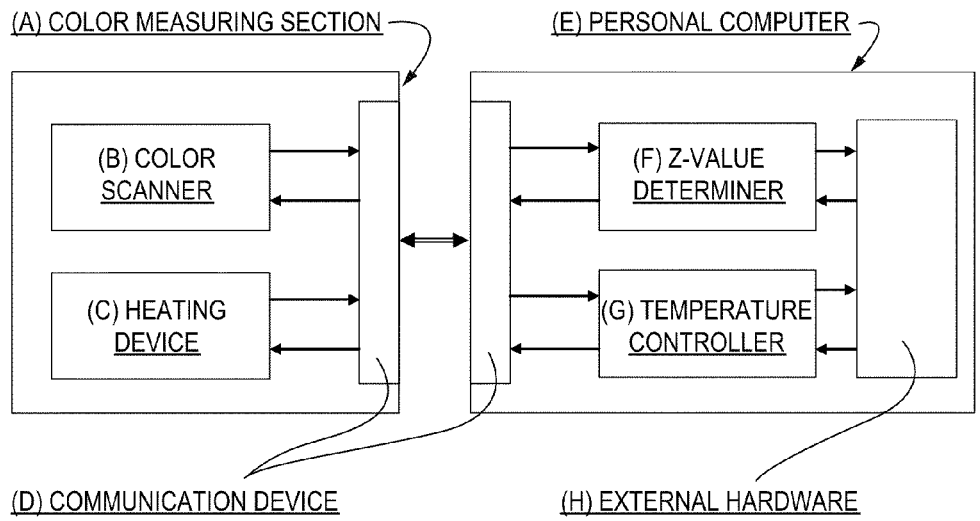
FIG. 1 is an overview of an example of the detection and incubation arrangement of the present invention.

The terms and abbreviations given below are used throughout this disclosure and are defined as follows.

The term 'assay medium' refers to a composition such as a solution, a solid or, preferably, in the form of a sol or a gel, for instance comprising a gelling agent. Suitable examples of gelling agents are agar, alginic acid and salts thereof, carrageenan, gelatin, hydroxypropylguar and derivatives thereof, locust bean gum (Carob gum), processed eucheuma seaweed and the like. However, the person skilled in the art will understand that other types of solid assay media may be based on carrier materials such as ceramics, cotton, glass, metal particles, paper, and polymers in any shape or form, silicates, sponges, wool and the like. Usually, an assay medium contains one or more indicators; however, these compounds may also be added later when the assay is being performed. The assay medium may comprise one or more types of assay organisms or enzymes as detecting agents and nutrients. Optionally, the assay medium may also contain one or more buffers, stabilizers, substances that change the sensitivity to certain analytes in a positive or negative way, and/or viscosity-increasing agents. Examples of substances that change the sensitivity to certain analytes are antifolates like ormethoprim, tetroxoprim and trimethoprim that improve the sensitivity of the assay organism towards sulfa compounds or salts of oxalic acid or hydrofluoric acid, which improve the sensitivity towards tetracycline. Examples of viscosity-increasing agents are ascorbyl methylsilanol pectinate, carbomer, carboxymethyl cellulose, cetearyl alcohol, cetyl alcohol, cetyl esters, cocamide DEA, emulsifying wax, glucose, hydroxyethyl cellulose, hydroxypropylmethyl cellulose, lauramide DEA, linoleamide DEA, magnesium aluminum silicate, maltodextrins, PEG-8 distearate, polyacrylamide, polyvinyl alcohol, PVP/hexadecene copolymer, sodium chloride, sodium sulfate, soyamidopropyl betaine, xanthan gum and the like. The assay medium may be contained within any type of container; frequently used containers are tubes, microtiter plates and Petri dishes.

The term 'CFU' is an abbreviation of Colony Forming Units and refers to the number of microorganisms, spores of microorganisms, partially germinated spores of microorganisms or vegetative cells capable of producing colonies of microorganisms.

The term 'reader' refers to a device capable of capturing color or other spectral images and translating these images into analogous or digital signals, such as a scanner, a digital photo camera or video camera, a web cam apparatus or the like.

The term 'fluid' refers to a substance (as a liquid, not a gas) tending to flow or conform to the outline of its container.

The term 'gelling agent' refers to a compound that assists in changing a mixture into or taking on the form of a gel.

The term 'indicator' refers to a substance used to measure (for example by change of color or fluorescence) the condition of an assay medium with respect to the presence of a particular material (for example an acid, a base, oxidizing or reducing agents). For instance, the term 'indicator' may refer to one or more compounds that are known as pH-indicators, but also to one or more compounds that are known as redox-indicators. Also, the term 'indicator' may refer to mixtures of two or more different types of indicators, such as a combination of a pH- and a redox-indicator. In general, when two or more indicators are used, these indicators are co-operating to increase the indicator effect of each of the indicators when taken alone.

The term 'sensitivity' refers to the degree of receptiveness of a given system to sense a certain state. More particularly, in the present case 'sensitivity' refers to the degree by which concentrations of analytes in a sample can be determined.

The term 'spore' refers to a primitive usually unicellular often environmentally resistant dormant or reproductive body produced by microorganisms and capable of development into a new individual microorganism.

The term 'temperature profile' refers to a range of temperature values as a function of time. This may be a linear range, a hyperbolic range, an exponential range, a polynomial range but also any range suitable for a specific application and not necessarily described by a simple mathematical function. A pre-set temperature is a species of the genus temperature profile as it is one temperature value maintained the same throughout time.

The term 'threshold' refers to the concentration value above which a given analyte is to be regarded as present (positive) and below which said analyte is to be regarded as absent (negative). Generally, a threshold value is given for particular analytes in particular samples by local, regional or interregional authorities but it can also be pre-set for certain research purposes. Alternatively, a threshold value may be a derivative of a formula, such as a slope.

The term 'transparent' refers to any material that allows for light to travel through the material. Ideally a transparent material does not retain any proportion of the light as it is send in, however since such material is not known, the term 'transparent' particularly refers to materials that allow for light to travel through with minimal losses. Minimal losses may be in the range below $50\%.\text{mm}^{-1}$, preferably below $20\%.\text{mm}^{-1}$, more preferably below $10\%.\text{mm}^{-1}$, still more preferably below $5\%.\text{mm}^{-1}$, most preferably below $1\%.\text{mm}^{-1}$.

In a first aspect of the present invention there is provided a detection arrangement for detecting presence and concentration of an analyte in a sample, comprising a processor, a memory, a display, a communication device such as a corn port or USB port and a spectrum measuring device, said memory, said display and said measuring device being arranged to communicate with said processor and arranged to generate light signals, to send said light signals to said sample, to receive light signals from said sample, to convert said light signals into color signals and to send these color signals to the processor whereby a means is present for maintaining a constant temperature or temperature profile of said sample. Such a means may be an incubator comprising a heating device and an aperture for holding a sample. Either the measuring device is located within the heating device or the heating device is located within the measuring device. Although the detection arrangement may comprise generation of light signals at one source followed by detection of light signal at a source opposite the first source, in a preferred embodiment, the detection arrangement avoids the problems associated with the traveling of light through sample and substrate as it is based on the principle of reflection of light. Hence, using reflection of light, it is for instance no longer required to remove the sample from the substrate prior to irradiation, which in turn has the advantage that a broader part of the fight spectrum (i.e. also including infrared) can be used. Moreover, the above can be realized using easily accessible and relatively cheap equipment such as a digital camera, a scanner, a web-cam or the like.

In a first embodiment of the invention, said means for maintaining a constant temperature or temperature profile of a sample and an assay medium is a device comprising one or more apertures for holding assay medium and/or samples. Samples and/or assay medium may be introduced directly into the apertures but alternatively can also be present in containers of which at least the bottom is transparent. The device has a transparent bottom side, at least at those places where sample and/or assay medium are located. Temperature maintenance is realized by constructing at least part of the device from a material that warms up when an electrical current is applied, or alternatively by constructing at least part of the device from a material through which a fluid with a pre-set temperature can be circulated. As an example, said means for maintaining a constant temperature or temperature profile of the sample and/or assay is a transparent plate, for instance made of glass or any kind of plastic. The transparent plate is coated with a material that can be heated, for instance by applying an electrical current. Advantageously, said material is transparent or semi-transparent. In the latter case the material will allow light to travel through when applied in a sufficiently thin layer, preferably having a thickness ranging from 0.01-200 μm, more preferably ranging from 0.1-50 μm, most preferably ranging from 1-20 μm, still most preferably ranging from 5-15 μm. Titanium dioxide is a material that is particularly suitable for obtaining the desired effect, but also other materials known in the art may be used. The size of the particles preferably ranges from 0.1-100 nm, more preferably from 1-50 nm, most preferably from 10-30 nm. In order to heat the material and hence the plate supporting the samples to be analyzed, a means for applying an electrical current is attached to the plate. Such a means may be a set of electrodes attached to the plate and contacted with the material. The electrodes can be made of any material that allows for transport of electrical current; attachment of the electrodes can be effected with glue capable of transporting electrical current. Such electrodes and glues are well known to the person skilled in the art. Optionally, the temperature is measured by means of a temperature sensor similarly attached to the plate and connected to the processor. Optionally also the electrodes are connected to the processor and the processor is instructed to keep the temperature of the plate at a pre-set value or profile by applying the required current to the electrodes. Samples and/or assay medium may be introduced directly into the apertures of the heating device but alternatively can also be present in containers of which at least the bottom is transparent. The device has a transparent bottom side, at least at those places where sample and/or assay medium are located. Temperature maintenance is realized by constructing at least part of the device from a material that warms up when an electrical current is applied.

In another embodiment of the invention, said means for maintaining a constant temperature or temperature profile of a sample and an assay medium is a device comprising one or more apertures for holding assay medium and/or samples. Attached to said device are heat traces, for instance made from metals such as aluminum, copper, gold, lead, silver, tin and the like that allow for generating a specific heat input for homogeneous temperature gradients. To increase accuracy of the temperature gradient over the device, one or more temperature sensors and/or controllers are optionally included to adjust the current input. In an example, said temperature sensors are electrically integrated in a print plate and are in thermal contact with said device which is made of a heat conducting material, such as a metal like aluminum, copper or iron. The temperature is controlled by means of a Proportional Integral Derivative (PID) controller or any other type of controller or combination thereof. To increase speed of detection and reproducibility the heating device may be pre-heated at a higher temperature.

In the Figures and the legends thereto an example is given of the detection arrangement (FIG. 1) and the heating device (FIG. 2) of the present invention. Although these Figures are not intended as limiting the scope of the invention, they will allow the person skilled in the art to reproduce the invention.

In a second aspect of the invention there is provided a method for determining the presence or absence of an analyte in a fluid by analysis of image data from an assay that generates an image result on an assay medium. More specifically, said assay, together with a sample of the fluid to be analyzed, requires to be incubated at a pre-set temperature or temperature profile. Temperatures or temperature profiles depend on the nature of the assay. For instance, in microbiological inhibition assays, microorganisms usually require a temperature ranging from 25-45° C., preferably from 30-40° C., more preferably from 35-39° C. However, other microorganisms such as thermophilic microorganisms (i.e. Bacillus stearothermophilus and others) require quite different temperatures for optimal growth, i.e. ranging from 40-75° C., preferably from 50-70° C., more preferably from 60-68° C. and most preferably from 63-66° C. Advantageously, the method of the present invention provides for simultaneous incubation of the assay, obtaining an image result on an assay medium and imaging of the image result with an image acquisition device to generate analog and/or digital image data corresponding to the image result. Also simultaneously, a data processing means may be used to apply to the digital image data, a stored relationship between the image result and assay calibration data, such as a standard color card, in order to generate a quantified result for said assay. Alternatively, multiple measurements based on color differences in time may be used to obtain said quantified result. The latter alternative has the advantage that calibration may be circumvented.

In a first embodiment of the second aspect of the invention, a pre-set temperature or temperature profile is maintained by means for maintaining a constant temperature or temperature profile as outlined in the first aspect of the invention. Advantageously said means is heated at the same temperature at every point of said means. Preferably, the differences in temperature between individual points of said means are not more than 10° C., preferably not more than 5° C., more preferably not more than 2° C., and most preferably not more than 1° C.

In a second embodiment image results are obtained continuously or at regular intervals (i.e. at least twice and the time interval between two consecutive measurements is 0.00001 to 200 minutes) or at irregular intervals in order to establish any changes as early as possible. Preferably, said time interval is between 0.1 min and 160 min, more preferably between 0.5 min and 120 min, and most preferably between 1 min and 10 min. Measuring color values as a function of time offers several substantial advantages.

In the first place, many of the assays used in the art suffer the disadvantage of reducing durability. As a result of this, fixed assay duration inevitably leads to a lower accuracy. The reason for this is that, the older a given assay is, the longer it will take to obtain a certain result. Establishing the required test duration by means of running a blank sample may circumvent this, although this is a cumbersome methodology which still lacks optimal accuracy. By obtaining results as a function of time however, this drawback is now circumvented as the exact point in time where a given color parameter changes can now be measured precisely during the assay. Consequently, by using the method of the present invention, the assay storage life, although still an important parameter for the suitability of an assay per se, is no longer decisive for the accuracy of the assay.

In the second place, by taking measurements early during an assay, the sensitivity of the assay increases. For instance, in microbiological inhibition assays, growth inhibition of microorganisms occurs at lower analyte concentrations than later on during the assay when the inhibitory effect of the analytes begins to diminish. Advantageously, depending on the type of analyte, the results of microbial inhibition assays can be obtained in hitherto unprecedented short times, i.e. within 120 minutes, within 90 minutes or even within 60 or 30 minutes.

In the third place, rather than increasing the sensitivity by measuring early during an assay, the method of the present invention allows for further speeding up analysis times in microbial inhibition assays by increasing the amount of microorganisms. Whereas in prior art methods this approach would lead to decreasing sensitivity, measuring as a function of time as in the present invention makes it possible to counteract the decrease in sensitivity by shortening the assay duration. As an example, prior art microbial inhibition assays usually employ microorganism concentrations ranging from $10^4$-$10^9$ CFU.ml$^{-1}$, whereas in the present invention these concentrations can be increased without loss of sensitivity two-fold to even 1000-fold. Hence, suitable and fast assays can be achieved using microorganism concentrations up to $10^9, 5 \times 10^9, 10^{10}, 5 \times 10^{10}, 10^{11}$ or even $10^{12}$ CFU.ml$^{-1}$, giving assay durations ranging from 5-120 min, preferably 30-100 min, more preferably 45-90 min.

In the fourth place, the method of the present invention allows for the easy incorporation of more than one threshold value, for instance in order to satisfy multiple (governmental) requirements. For example, a threshold value can be associated with the slope of a color value vs. time relation (i.e. the second derivative) and likewise multiple threshold values can be associated with multiple slope values. This allows for measuring multiple sensitivities and/or multiple analytes.

In a third embodiment, a detection arrangement can be used comprising of a processor, a memory, a display, and a color measuring device, said memory, said display and said color measuring device being arranged to communicate with said processor, by generating light signals with said color measuring device, sending said light signals to said sample, receiving reflected light signals back from said sample, converting said reflected light signals into color signals and sending said color signals to said processor. Optionally, said color signals are manipulated in order to achieve a better separation between the color components of interest.

One example is adaptation of the color parameter of interest by means of a mathematical formula such as for instance those present in photographic manipulation programs known to the person skilled in the art. It has been shown that the use of such photographic manipulation programs results in a marked difference in color parameters thereby allowing for easier discrimination between various samples. This phenomenon results in earlier interpretation of the assay in question, thereby making the assay significantly faster than prior art assays.

Another example of a mathematical formula is the calculation of the value of a composite parameter with the aid of said processor. Such a parameter may be a parameter Z in accordance with a following equation:

$$Z = \sum_{i=1}^{n} w_i x_i$$

where $x_i$ is a color signal i and $w_i$ is a corresponding weighing factor and i is an index ranging from 1 to n and n is an integer equal to the number of color signals. In order to establish the ongoing changes in the assay, the following sequence of steps may be performed:
1) measuring the value of Z for each sample and determining the time $t_1$ at which said value Z is equal to a value $Z_1$ and the time $t_2$ at which said value Z is equal to a value $Z_2$;
2) calculating by means of said processor the difference $\Delta t$ between said time $t_1$ and said time $t_2$ according to the formula $\Delta t = t_2 - t_1$ A suitable color model for use in the present invention is the L*a*b model and said equation is:

$$Z = w_1 \cdot L + w_2 \cdot a + w_3 \cdot b$$

Typical examples of suitable values of $Z_1$ and $Z_2$ are between 30 and −30 provided that $Z_1$ is larger than or equal to $Z_2$. In addition, the above sequence may be expanded by calculating if $\Delta t$ is larger than $\Delta t_{ref}$ and if this condition is met assigning a positive assay result indicating that the concentration of said analyte is higher than a concentration A and if this condition is not met, assigning a negative assay result indicating that the concentration of said analyte is lower than a concentration B, wherein concentration A is smaller than concentration B.

Figure 4:
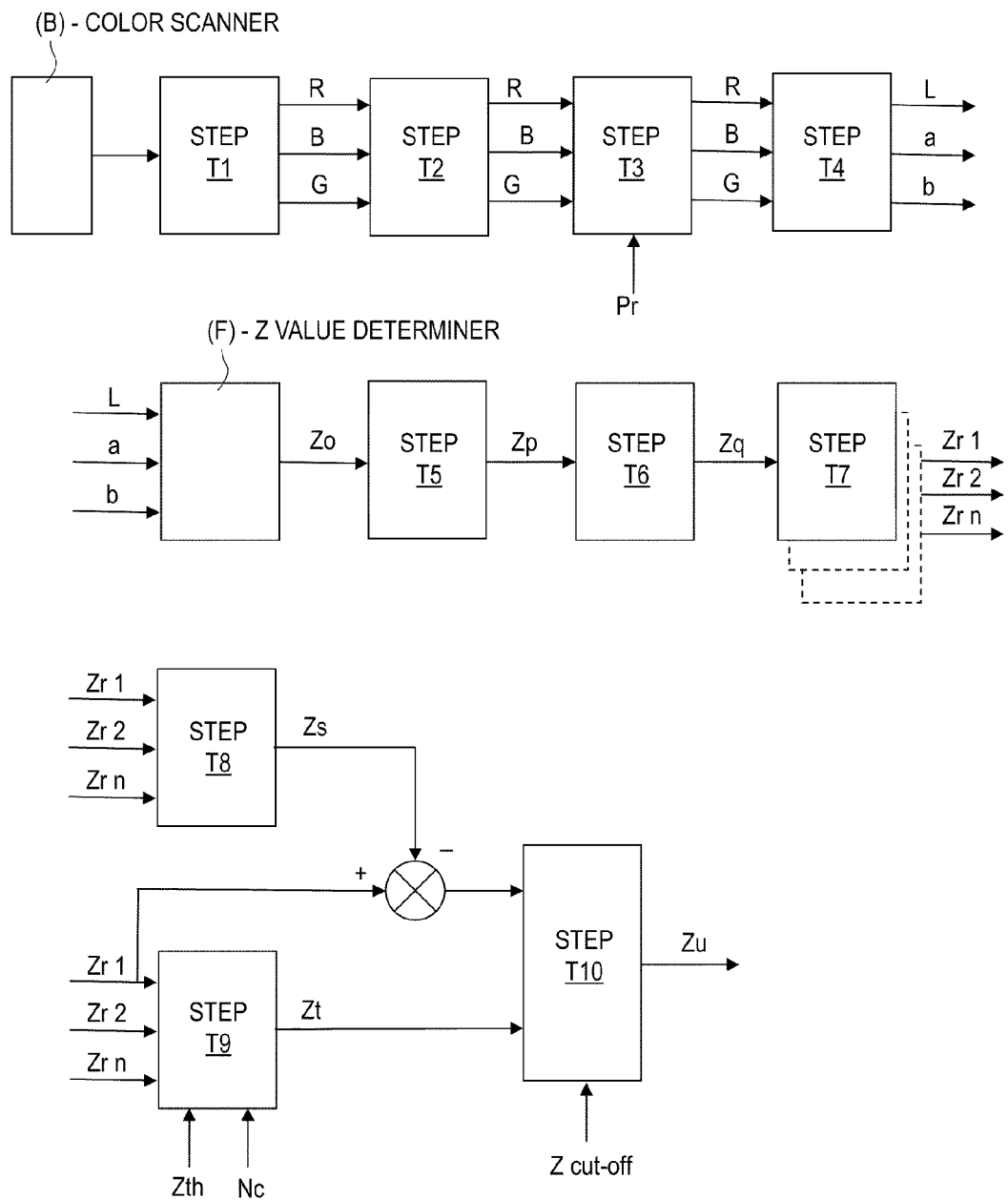
FIG. 4 is an overview of the sequence of steps to be carried out using the detection and incubation arrangement of the present invention.

In a most preferred example the detection arrangement of the present invention is used according to the scheme outlined in FIG. 4. The process from generating light signals to obtaining assay data is given in detail in the legend to FIG. 4.

In a fourth embodiment multiple samples may be employed, one of which may comprise a reference sample with a known amount (such as a threshold amount) of the analyte to be detected. Thus, at least two samples of different fluids are contacted with an assay medium comprising an assay microorganism and an indicator, incubated and monitored simultaneously and wherein the value $Z_1$ is set by said processor to be equal to the lowest Z-value of any of the samples provided said lowest Z-value is at least 10% and not more than 50% below the highest Z-value of any sample measured and wherein the value $Z_2$ is set by the processor to be equal to the lowest Z-value of the samples provided said lowest Z-value is at least 90% and not more than 200% below the highest Z-value of any sample measured.

In a fifth embodiment there is provided a method wherein $Z_1$ mentioned above is equal to $Z_2$, and $Z_t$ is the recorded value of Z at time t, and which method further comprises calculating by means of said processor parameters of a mathematical expression relating $Z_t$ to t, comparing the values of the parameters with those of a control sample in which the concentration of said analyte is known, and generating a signal indicating that the concentration of said analyte in said sample is higher than or equal to or lower than the concentration of said analyte in the control sample. Optionally, the parameters of a mathematical expression relating $Z_t$ to t in said control sample are pre-set in a computer program and/or obtainable by said processor from a remote processor by means of a network.

In a sixth embodiment there is provided a method for determining the presence or absence of an analyte in a fluid by analysis of image data from an assay that generates an image result on an assay medium. Said image results are obtained continuously at regular intervals and are compared with stored reference data. These stored reference data consist of e.g. spectral changing curves of several known analytes at different concentrations. A comparison of the stored and obtained data subsequently gives additional information concerning the type of analyte and the concentration of this analyte in the sample. It has surprisingly been found that the method of the present invention has the additional advantage that both various types of analytes and the concentration of the analytes in the sample can be detected simultaneously. Thus, by measuring spectral changing curves of known analytes and storing these curves in a processor, the specific assay results can be fitted to the stored data using a best-fit method and consequently the type and concentration of analyte can be deduced. Using the approach of this embodiment, a differentiation can be made between two or more different types of analytes, such as for instance β-lactam antibiotics and sulfa's, like for instance between penicillin and sulfadiazin.

LEGEND TO THE FIGURES

FIG. 1 is an overview of an example of the detection and incubation arrangement of the present invention. A is a section comprising a color measuring device B, for instance a scanner, a means C for maintaining a constant temperature or a temperature profile of the sample, such as a heating device comprising temperature sensors, and a communication device D. E is a (personal) computer comprising a communication device D, an algorithm for determination of the Z-value F, one or more temperature controllers G and software for interfacing with user(s) and/or external equipment H.

Figure 2:
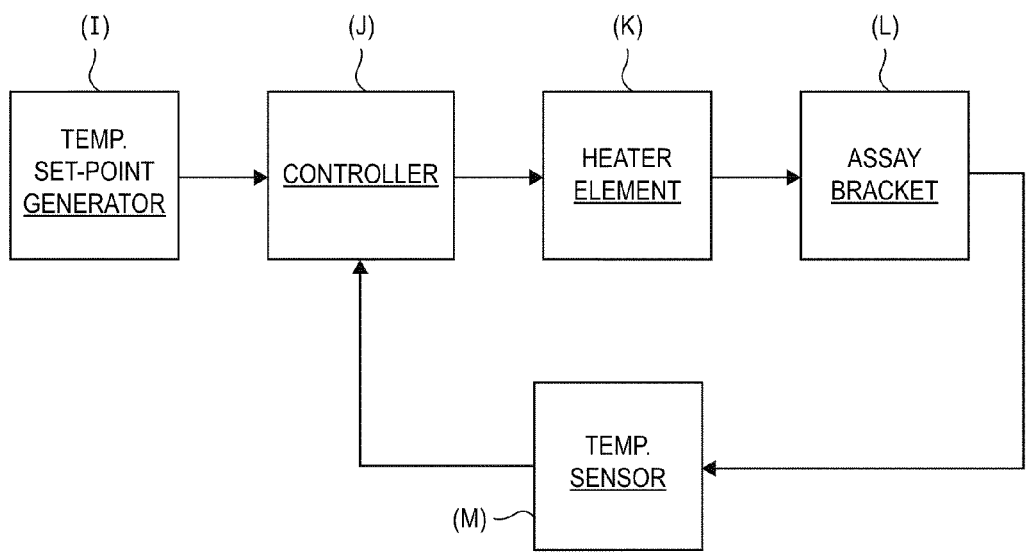
FIG. 2 is a detail of means C and G shown in FIG. 1.

FIG. 2 is a detail of means C and G described in FIG. 1 comprising a temperature set-point generator 1, a controller (for instance PID) J, a heater element K, an assay bracket L and a temperature sensor M. To increase temperature accuracy means J up to and including M can be build up several times.

Figure 3:
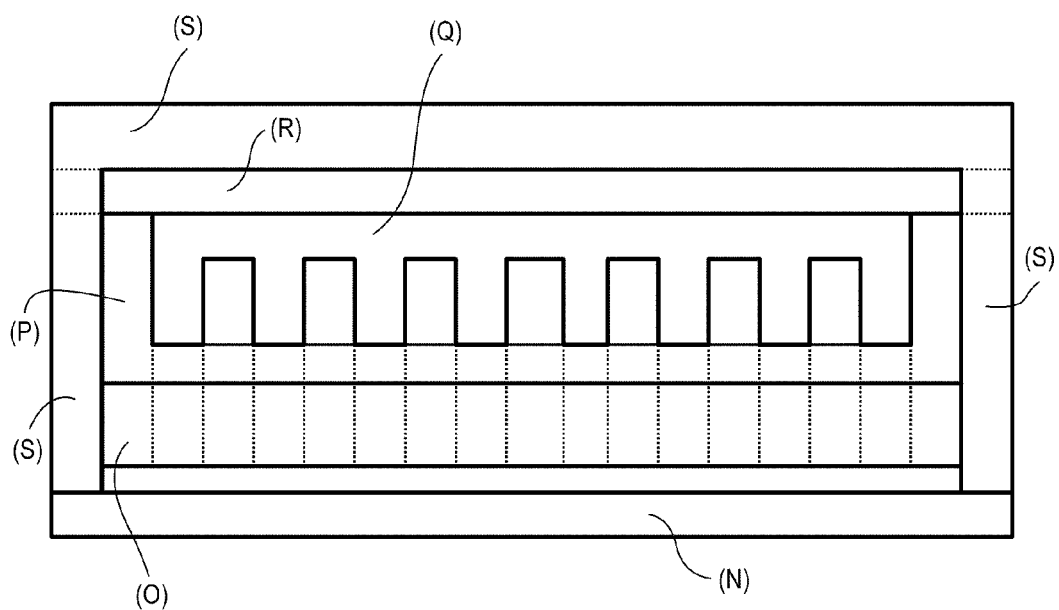
FIG. 3 is a cross-sectional overview of an example of a heater device and assay bracket shown in FIG. 2.

FIG. 3 is a cross-sectional overview of an example of a heater device and assay bracket as described in FIG. 2 comprising a glass panel N, a heater O, a bracket P, an assay Q, a second heater R and insulation material S.

FIG. 4 is an overview of the sequence of steps to be carried out using the detection and incubation arrangement of the present invention.

In T1, after each measurement the image from color measuring device B is depicted as a set of pixels. Each pixel contains three color signals: Red, Green and Blue (RGB). Pixel color can be expressed as RGB but other color spaces can be used too, for example Cyan, Magenta, Yellow, and Key (CMYK), XYZ and Hue, Saturation and Value (HSV). The exact location of the assay is determined using technology that is well-known to the person skilled in the art, for instance such as described in WO 2003/034341. Next, a representative sample of an area of the assay is taken and results in a matrix of n*m pixels (n and m are preferably in the range of 1-1000, more preferably from 3-100, depending on the size of the assay; suitable examples of n*m are 20*40, 100*100, 60*40, 20*20, most preferably 9*9). Other shape possibilities to determine a representative sample are circular, oval or a free set of pixels. The final result of T1 is a set of pixels for each assay; each set contains RGB data representing the color and luminance information of the selected pixels.

In T2, all assay data are transferred into one representative combination of RGB information. Examples of suitable methods are calculating the mean or median.

In T3, depending on the optical measuring device and set-up, color information may be calibrated. Already known calibration methods, such as using color reference cards, can be applied. A calibration cycle results in a calibration profile (Pr) that is input to a correcting algorithm. In the current example an ICC (intraclass correlation coefficient) profile is used. Other calibrations methods may be used too. The result of T3 is a set of corrected color signals RGB for the assay to be measured.

In T4 the RGB data is converted to the Lab color space using known methods.

F is the algorithm mentioned under FIG. 1 for calculating the Z-value: $Z = w_1 \cdot L + w_2 \cdot a + w_3 \cdot b$ T5 is an optional adaptation of the individual assay Z values based on assay position and Z-value.

Optionally, in T6, for each assay successive samples may be taken and smoothed, for example to exclude outliers and noise reduction. Smoothing can be achieved by known methods such as moving average or calculating the median from a number of samples.

Optionally, in T7, in order to further reduce noise, a curve fit may be applied onto consecutive samples. Examples of applicable curves are polynomial, exponential and logarithmic types. A preferred curve is a second degree polynomial curve.

Optionally, in T8, in order to compensate for possible unfavorable assay effects, due for instance to storage conditions, a normalizing step may be used. Initially the compensation value Zs is 0, after m measurements the correction value Zs can be calculated as follows:

$$\sum_{i=1}^{60}\sum_{j=1}^{96}\frac{Z_{ij}}{(60*96)}$$

wherein j is the number of assays, i the number of samples over which the plate is normalized. Index i ranges from 1-120, preferably 10-90, most preferably 40-60 (the value 60 is given as an example in the formula).

Function T9 is to determine when at least the required number of assays (Nc) shows a negative result (Zr<Zth and Zth<Zcut-off). As soon as this criterion is reached the results (positive or negative) of each individual assay can be determined by T10.

In T10, when indicated by T9 the final results Zu of each assay Zr can be determined. The result is positive if Zr≧Zcut-off and negative otherwise. When two different cut-off values are applied, an additional result indicated as doubtful can be obtained too.

The conversion of RGB values to Lab and Z including further processing to the final result Zu, is not limited to the sequence as described above. In an alternative the RGB or Lab values can be used directly to determine the final result.

Figure 5A:
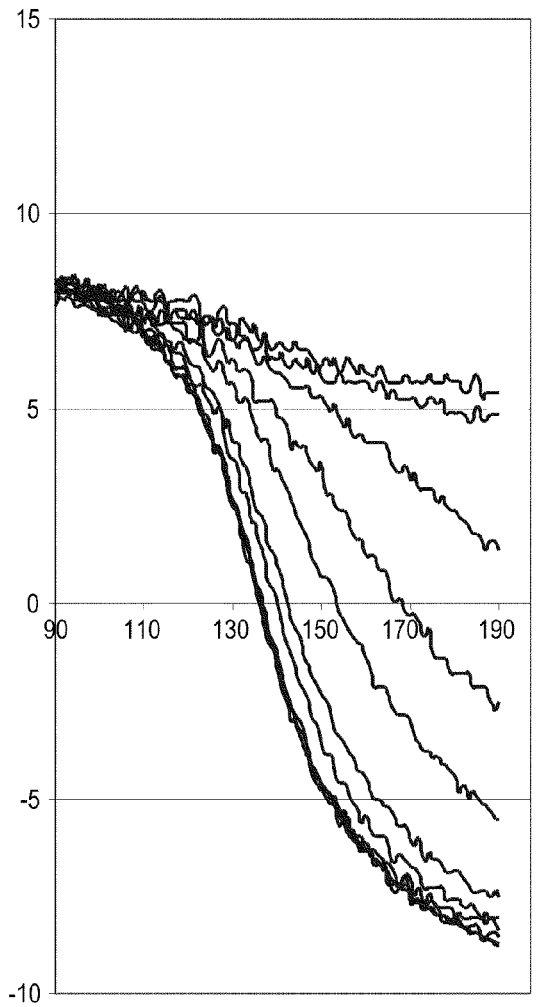
FIGS. 5A and 5B respectively show the differences in color profiles for penicillin G and sulfadiazine as a function of assay duration.
Figure 5B:
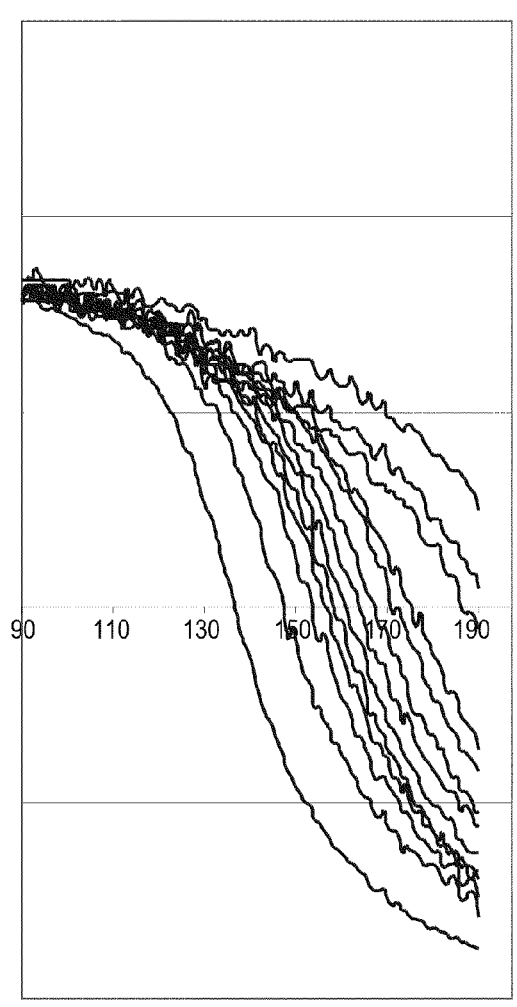
Figure 6:
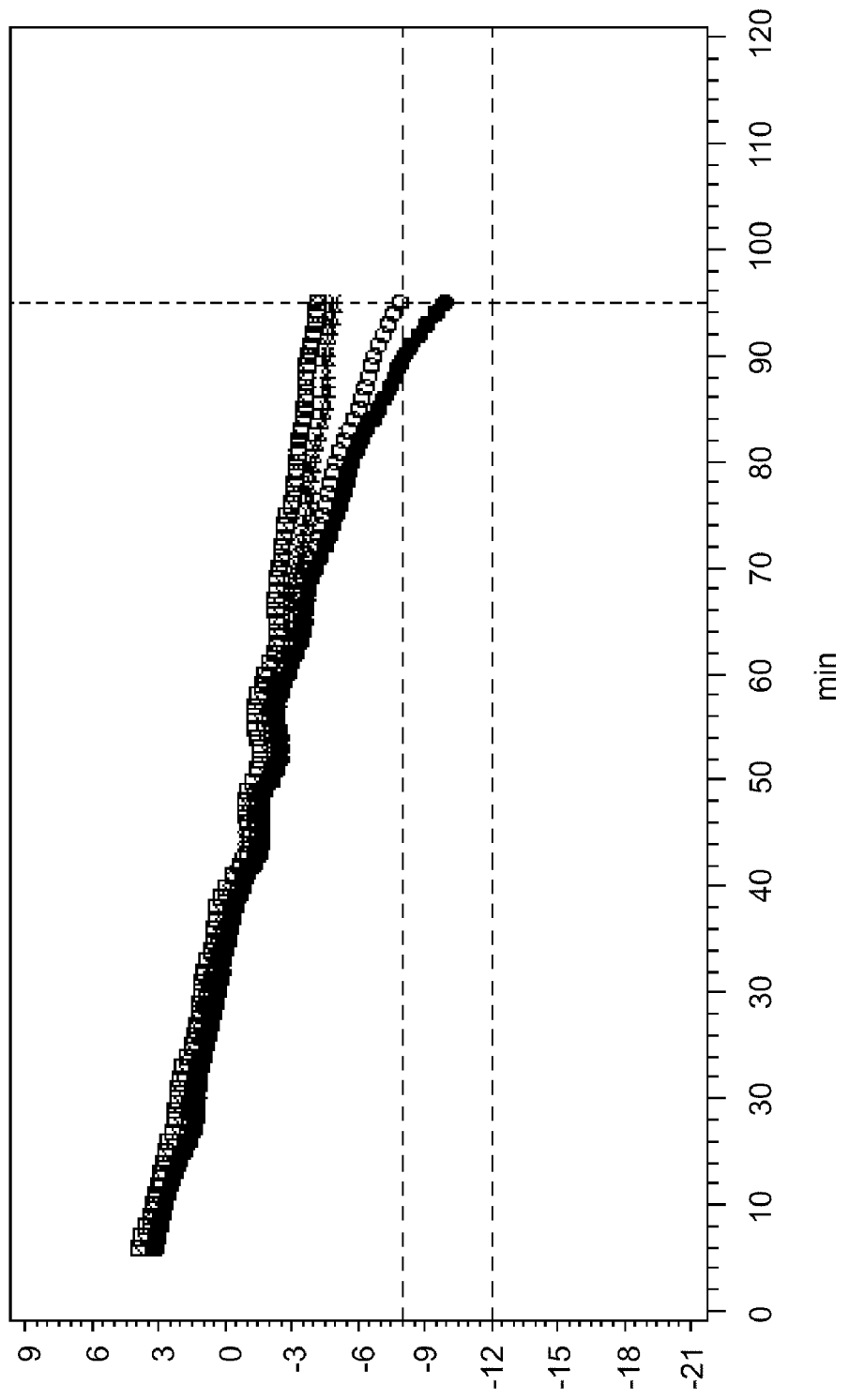
FIGS. 6-12 respectively show the differences in color profiles for penicillin G, sulfadiazine, amoxicillin, ceftiofur, cloxacillin, oxytetracyclin and erythromycin.
Figure 7:
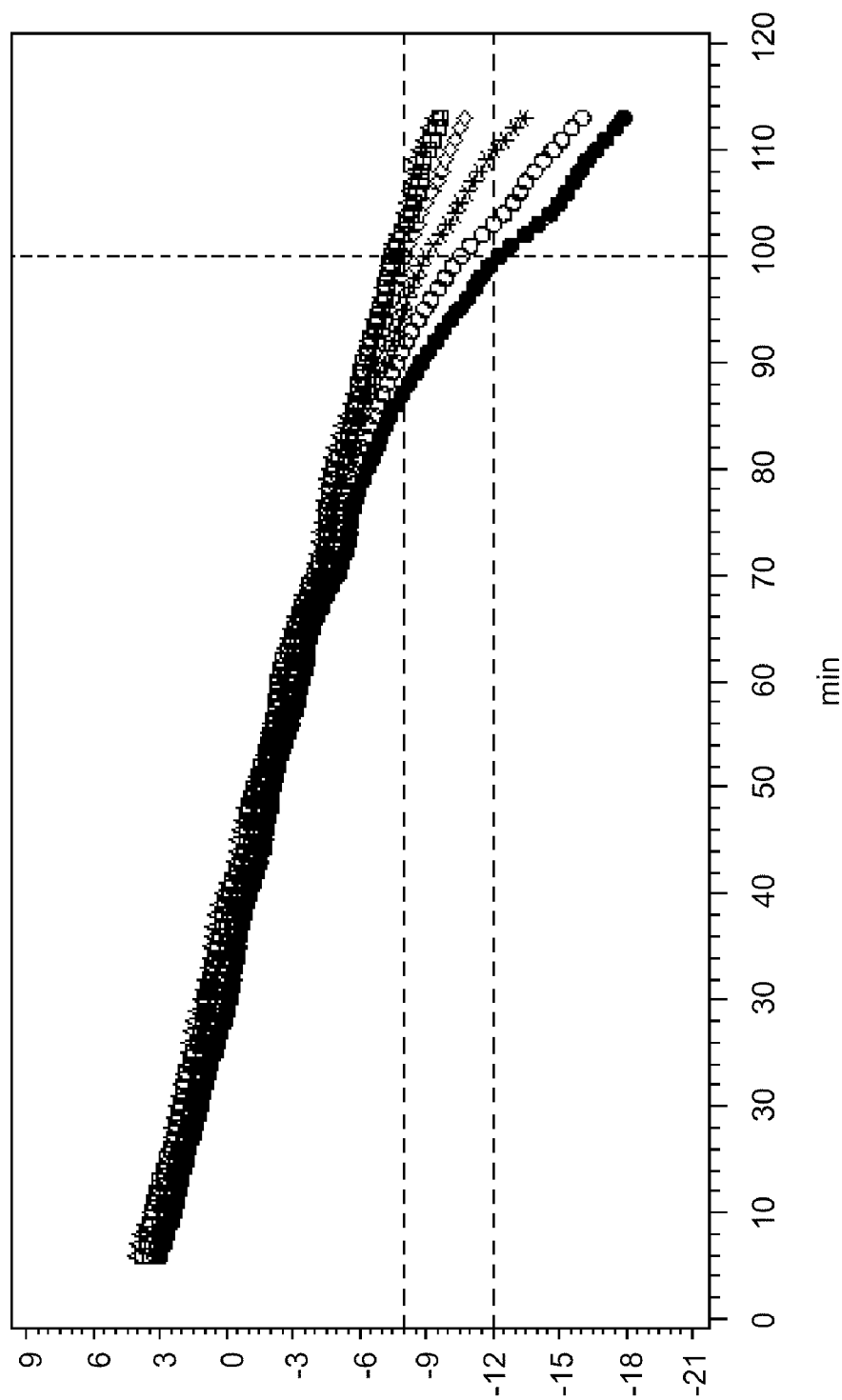
Figure 8:
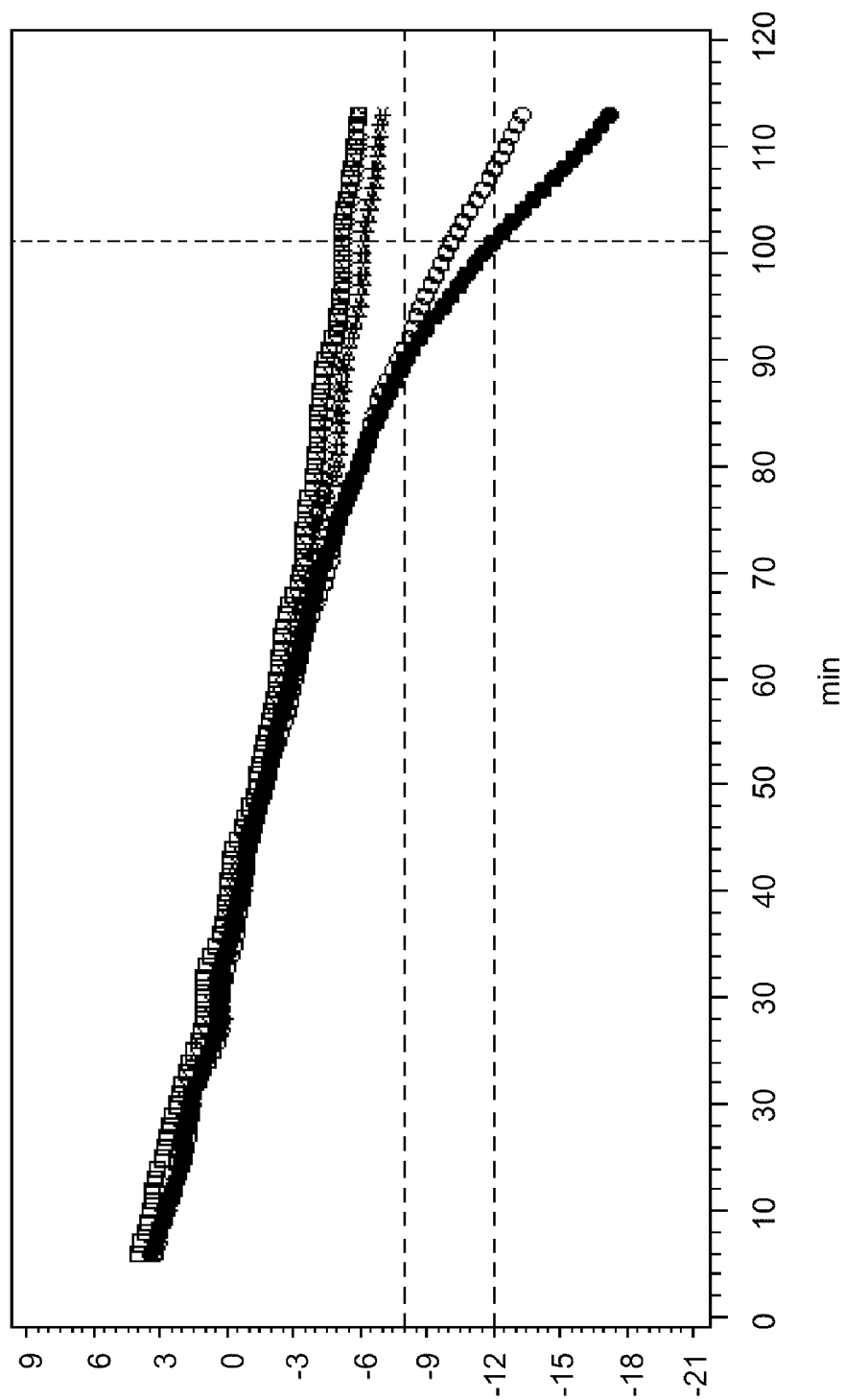
Figure 9:
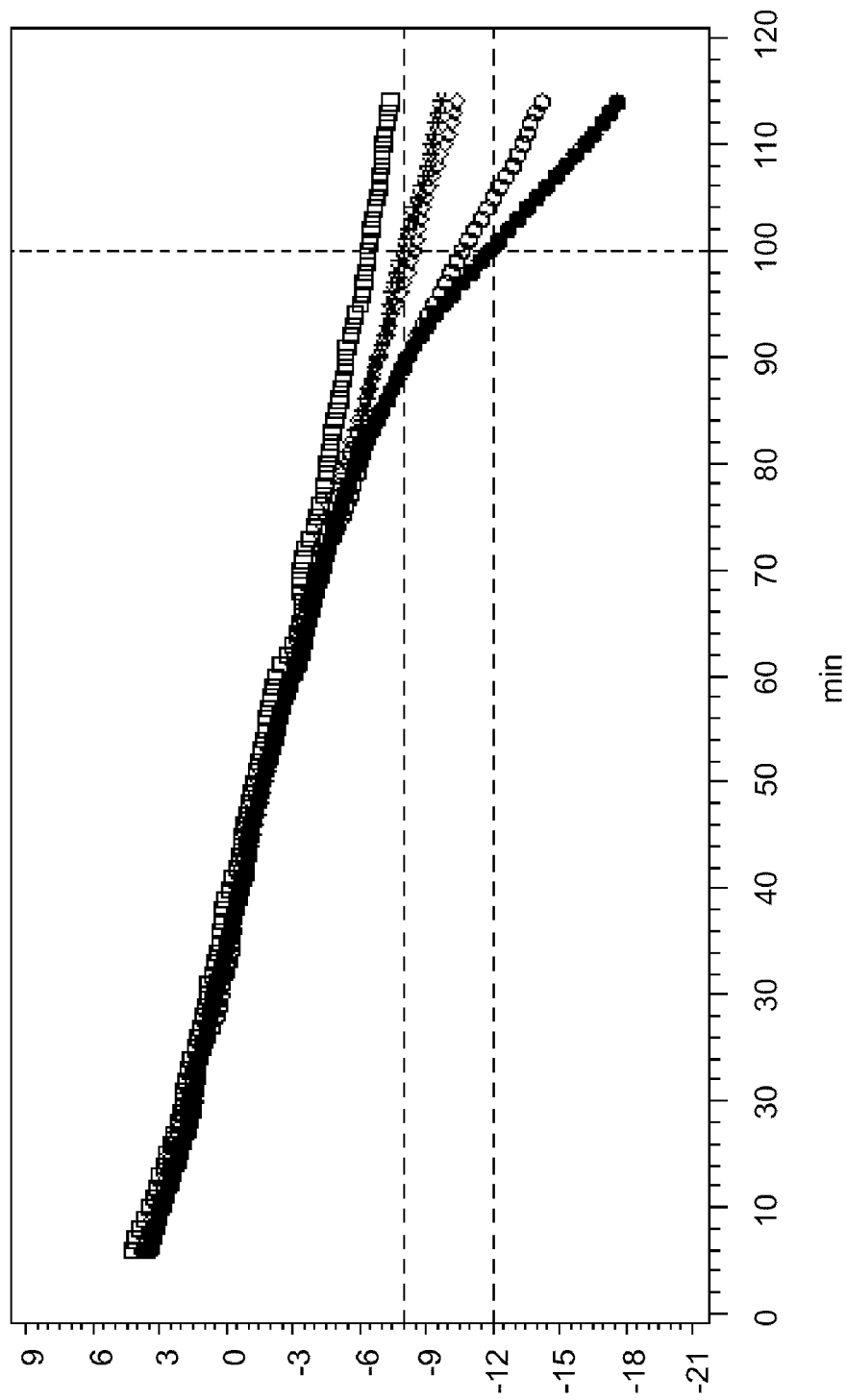
Figure 10:
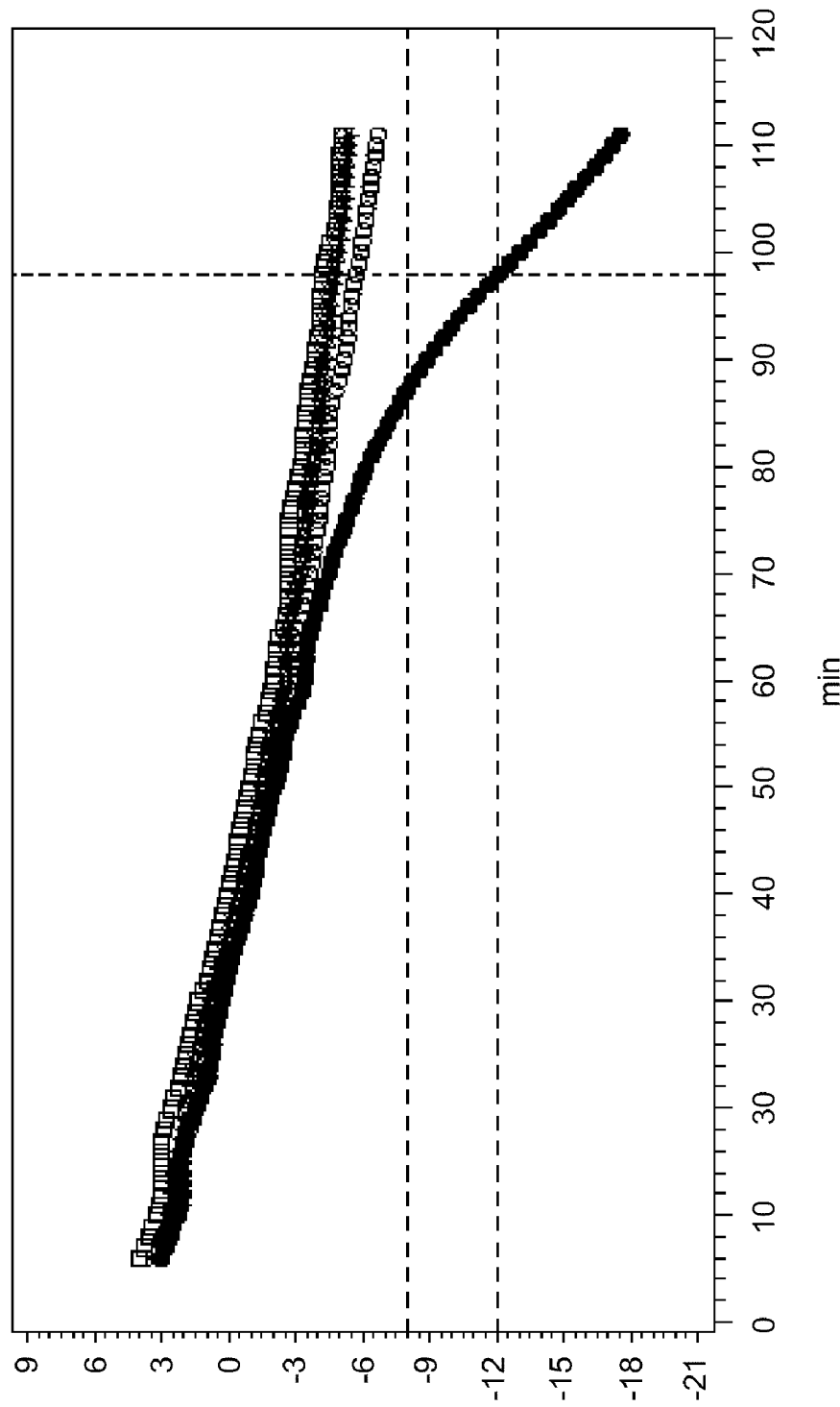
Figure 11:
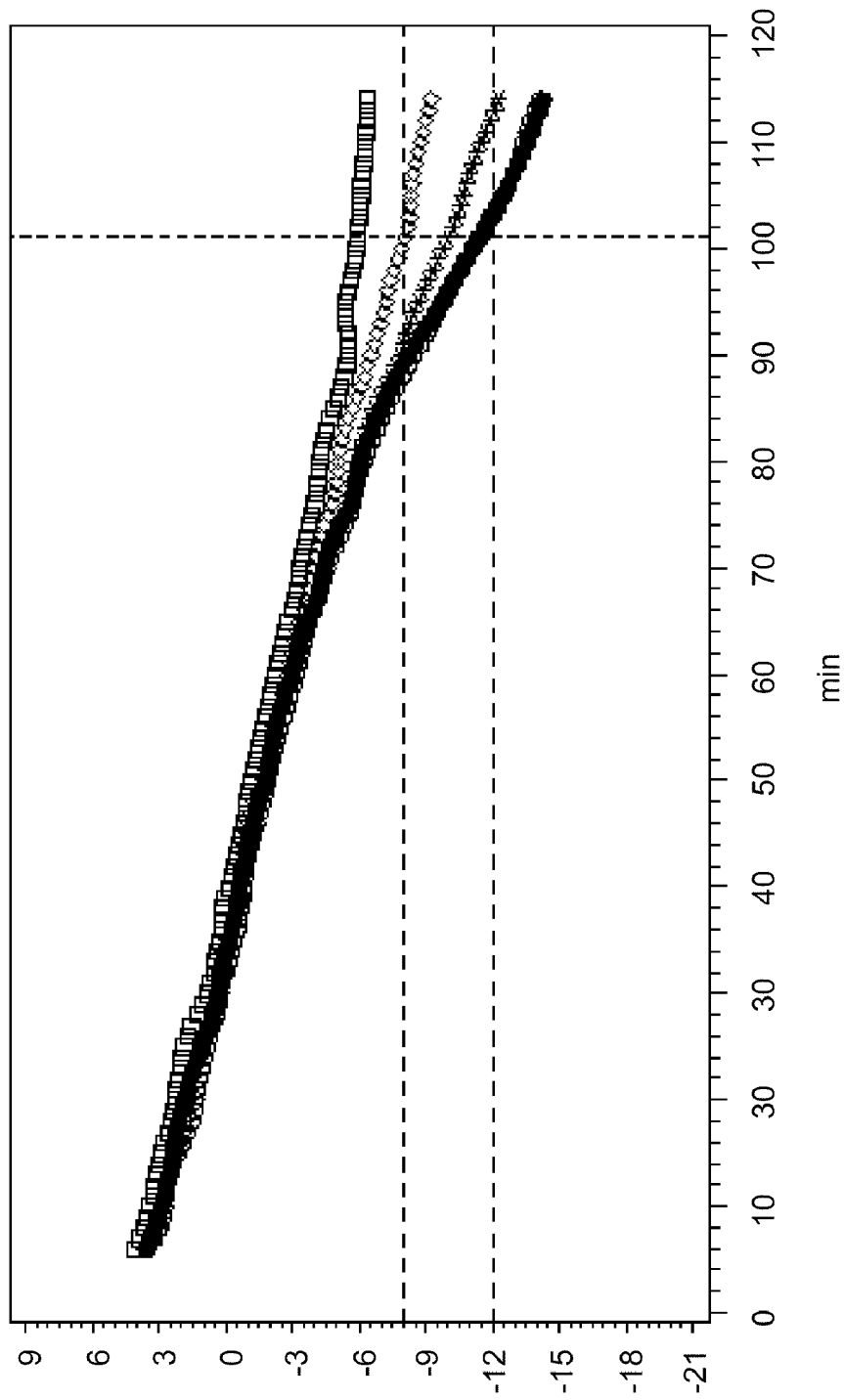
Figure 12:
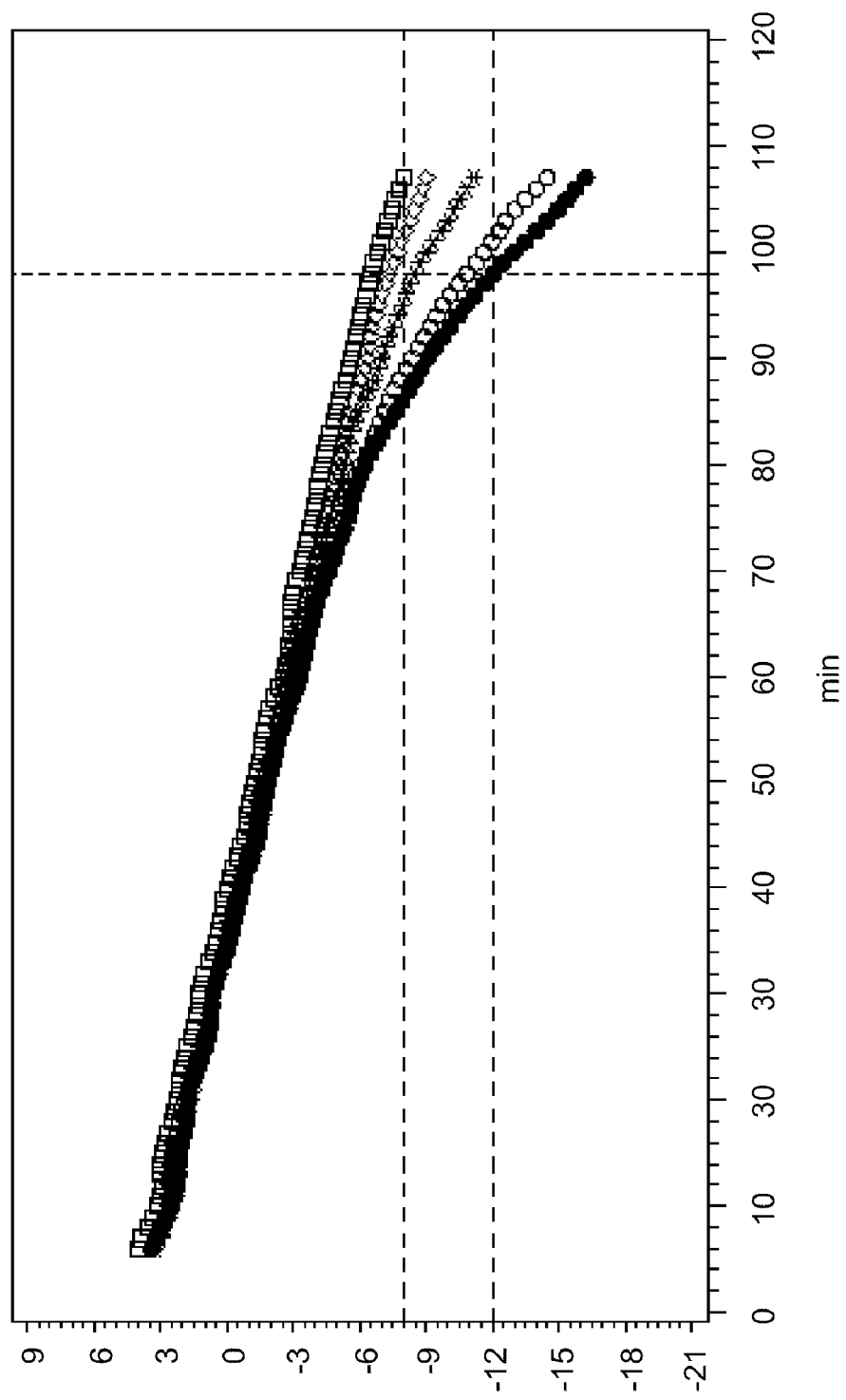

FIG. 5 shows the differences in color profiles (expressed as Z-value, y-axis) for penicillin G (5A, left panel) and sulfadiazine (5B, right panel) as a function of assay duration (x-axis, in minutes). The curves in FIG. 5A relate to samples containing, going from the lowest graph to the highest graph, 0, 0.4, 0.6, 0.8, 1, 1.2, 1.6, 2, 2.4, 2.8 and 3.2 ppb penicillin G. The curves in FIG. 5B relate to samples containing, going from the lowest graph to the highest graph, 0, 20, 40, 50, 60, 70, 80, 100, 120, 140, 200, 300 and 400 ppb sulfadiazine. The following equation was used: Z=0.35.a−0.65.b.

FIGS. 6-12 show the differences in color profiles (expressed as Z-value, y-axis) for seven antibiotics mentioned in the table below. The Z-value is shown as a function of assay duration (x-axis, in minutes). The curves in these Figures relate to samples containing the antibiotics in increasing concentrations (in ppb, see table). As outlined in the detailed description, the following equation was used: Z=0.35.a−0.65.b.

| Figure number | Antibiotic | Graph symbol (concentration in ppb) | | | | | |
|---|---|---|---|---|---|---|---|
| | | ● | ○ | X | ◆ | ■ | ▲ |
| 6 | Penicillin G | 0 | 1 | 2 | 3 | 4 | |
| 7 | Sulfadiazin | 0 | 25 | 50 | 100 | 150 | 200 |
| 8 | Amoxicillin | 0 | 2 | 3 | 4 | 5 | |
| 9 | Ceftiofur | 0 | 50 | 100 | 150 | 250 | |
| 10 | Cloxacillin | 0 | 15 | 30 | 60 | 120 | |
| 11 | Oxytetracyclin | 0 | 100 | 200 | 300 | 400 | |
| 12 | Erythromycin | 0 | 25 | 50 | 100 | 250 | |

EXAMPLES

Example 1

Determination of Color Values of in Commercially Available Microbial Inhibition Test for Two Different Antibiotics Using the scanning technology outlined in the second aspect of the invention, the color values in a commercially available microbial inhibition test (DSM DelvoTest®) were determined for a range of concentrations of penicillin G and sulfadiazin using the composite function $Z=w_L.L+w_a.a+w_b.b$. Samples were kept at 64° C. by using a titanium dioxide coated glass plate (obtained from Mansolar, www.mansolar.nl) equipped with a temperature sensor connected to a processor and two electrodes. The electrodes were connected to a 12 V power supply that was driven by the processor. The results of these experiments are shown in FIG. 5, showing that the curves for penicillin G and sulfadiazine differ substantially in shape. By relating these shapes to curves stored in the memory of the processor, various analytes (here penicillin G vs. sulfadiazine) can be distinguished. Next to that, FIG. 5 also discloses, for instance for sulfadiazine, that a difference between a 0 ppb sample and a 20 ppb sample can be observed already after 110 min, whereas prior art methods would have needed at least 150 min when an analyte-free sample reaches the Z=−5 to −10 region (where the color changes to yellow).

Example 2

Determination of Color Values of in Commercially Available Microbial Inhibition Test Using Photographic Manipulation Programs Using the scanning technology outlined in the second aspect of the invention, the color values in a commercially available microbial inhibition test (DSM DelvoTest®), were determined for a range of concentrations of penicillin G, sulfadiazin and oxytetracyclin by analysis using Adobe Elements as photographic manipulation program as follows. The image obtained from the scanner was stored as .jpg file and opened in Adobe Elements. Using the darkpoint marker a positive test was assigned and using the lightpoint marker a negative test was assigned. Subsequently the hue-value was adjusted to a value higher than 0 (preferably 10-30) and the saturation was also adjusted to a value higher than 0 (preferably 100). Next the color values were determined using the formula Z=0.35.a−0.65.b. From the table below it becomes clear that, using the photographic manipulation program, assay duration of 45 min with sensitivities of 3 ppb penicillin G, 200 ppb sulfadiazin and 200 ppb oxytetracyclin could be achieved.

| Using photographic manipulation | Assay duration (min) | Penicillin G (ppb) | Sulfadiazin (ppb) | Oxytetracyclin (ppb) |
|---|---|---|---|---|
| No | 52 | >6 | >300 | >500 |
| Yes | 45 | 3 | 200 | 200 |

Example 3

Determination of Color Values of in Commercially Available Microbial Inhibition Test for Two Different Antibiotics Using the scanning technology (shown in FIGS. 1-3) and outlined in the second aspect of the invention, the color values in a commercially available microbial inhibition test DSM DelvoTest®, were determined for a range of concentrations of penicillin G, sulfadiazin, ceftiofur, amoxicillin, cloxacillin, oxytetracyclin and erythromycin using the composite function $Z=w_L.L+w_a.a+w_b.b$.

| Antibiotic | Sensitivity Example 3 (in ppb, after 105 min) | Sensitivity DelvoTest ® SP-NT (in ppb, after 150 min) |
|---|---|---|
| Penicillin G | 2 | 1-2 |
| Sulfadiazin | 50 | 25-50 |
| Amoxicillin | 3 | 2-3 |
| Ceftiofur | 100 | 25-50 |
| Cloxacillin | 15 | 20 |
| Oxytetracyclin | 200 | 250-500 |
| Erythromycin | 100 | 40-80 |

Samples were kept at 64° C. using a plate with holes. Heat traces are divided over the plate, which allows generating a specific heat input related to the position, for homogeneous temperature gradients. To increase accuracy of the temperature gradient over the plate, temperature sensors and controllers were used to adjust the current input. Temperature was controlled by means of a PID. To increase speed of detection and reproducibility the heating device was pre-heated at a temperature of 80° C. The results of these experiments are shown in FIGS. 6-12 and the table above, showing that for said antibiotics the required concentration detection limits are obtainable within 105 minutes, whereas prior art methods, such as DelvoTest® SP-NT would have needed at least 150 min, when an analyte-free sample reaches the $Z=-5$ to $-12$ region (where the color changes to yellow).

The invention claimed is:

1. A detection arrangement for detecting presence of an analyte in a sample, comprising a processor, a memory, a display, a color measuring device, and means for maintaining a constant temperature or a temperature profile of said sample, said memory, said display and said color measuring device being arranged to communicate with said processor, said color measuring device being arranged to generate light signals, to send said light signals to said sample, to receive return light signals from said sample, to convert said return light signals into color signals and to send said color signals to said processor, said processor being operated by instructions stored in said memory and being arranged to calculate a value of a composite parameter Z in accordance with a following equation:

$$Z = \sum_{i=1}^{n} w_i x_i$$

where $x_i$ is a color signal i and $w_i$ is a corresponding weighing factor and i is an index ranging from 1 to n and n is an integer equal to the number of color signals, wherein
the means for maintaining a constant temperature or a temperature profile of said sample is a transparent plate coated with titanium dioxide to which electrodes are attached.

2. A method for determining the presence or absence of an analyte in a fluid by analysis of image data from an assay that generates an image result on an assay medium, comprising the steps of:
(a) incubating a sample of said fluid together with said assay at a pre-set temperature or temperature profile by means of a transparent plate coated with titanium dioxide to which electrodes are attached;
(b) obtaining said image result on an assay medium; and
(c) imaging the image result with an image acquisition device to generate digital image data corresponding to the image result; and
(d) using data processing means, applying to the digital image data a stored relationship between the image result and assay calibration data to generate a quantified result for said assay, wherein incubation step (a) is carried out simultaneously with steps (b)-(c).

3. The method according to claim 2, wherein multiple image results are obtained continuously or at regular intervals in time.

4. The method according to claim 2 further comprising photographic manipulation.

5. The method according to claim 2 wherein the following steps are performed:
(a) measuring a value of Z for each sample and determining the time $t_1$ at which said value Z is equal to a value $Z_1$ and the time $t_2$ at which said value Z is equal to a value $Z_2$; and
(b) calculating by means of said processor a difference $\Delta t$ between said time $t_1$ and said time $t_2$ according to the formula $\Delta t = t_2 - t_1$.

6. The method according to claim 2, wherein said quantified result is generated in less than 120 minutes.

* * * * *